United States Patent [19]

Fukada

[11] 4,065,261
[45] Dec. 27, 1977

[54] DEVICE FOR EMITTING VOLATILE SUBSTANCE

[75] Inventor: Rokuro Fukada, Ohtsu, Japan

[73] Assignee: Eikosha Co., Ltd., Kyoto, Japan

[21] Appl. No.: 694,559

[22] Filed: June 10, 1976

[51] Int. Cl.² .......................... A61L 9/01; A61L 9/04
[52] U.S. Cl. ..................................... 21/74 R; 21/103; 21/122; 21/126; 239/58; 261/95
[58] Field of Search .................. 21/53, 55, 74 R, 122, 21/126, 103; 239/57, 58, 59, 60; 261/95, 99, 102, 104

[56] References Cited

U.S. PATENT DOCUMENTS

| 1,238,068 | 8/1917 | Slater et al. | 21/74 R |
|---|---|---|---|
| 1,963,501 | 6/1934 | Mitchell | 239/57 X |
| 2,247,600 | 7/1941 | Brennan et al. | 239/57 |
| 2,614,820 | 10/1952 | Boydjieff | 21/126 X |
| 2,763,395 | 9/1956 | Meek | 239/58 X |
| 2,797,844 | 7/1957 | Meek | 239/60 X |
| 3,528,781 | 9/1970 | Gelfman et al. | 21/74 R X |
| 3,595,607 | 7/1971 | Gores | 21/74 R |
| 3,946,945 | 3/1976 | Odioso et al. | 239/58 |

Primary Examiner—Joseph Scovronek
Assistant Examiner—Arnold Turk

[57] ABSTRACT

A method for emitting volatile substance comprising passing air in one direction into a cylinder inserted into a container wherein is held a solid material containing volatile substance, whereby air may be in contact with the solid material while passing through said container, and a device for carrying out the method comprising the solid material containing volatile substance, the container for holding the solid material, the cylinder inserted into the container, a fan for sucking air into the cylinder to form an air stream axially flowing upward relative to the device, a motor for effecting the rotation of the fan, and an electric circuit for activating the motor.

7 Claims, 10 Drawing Figures

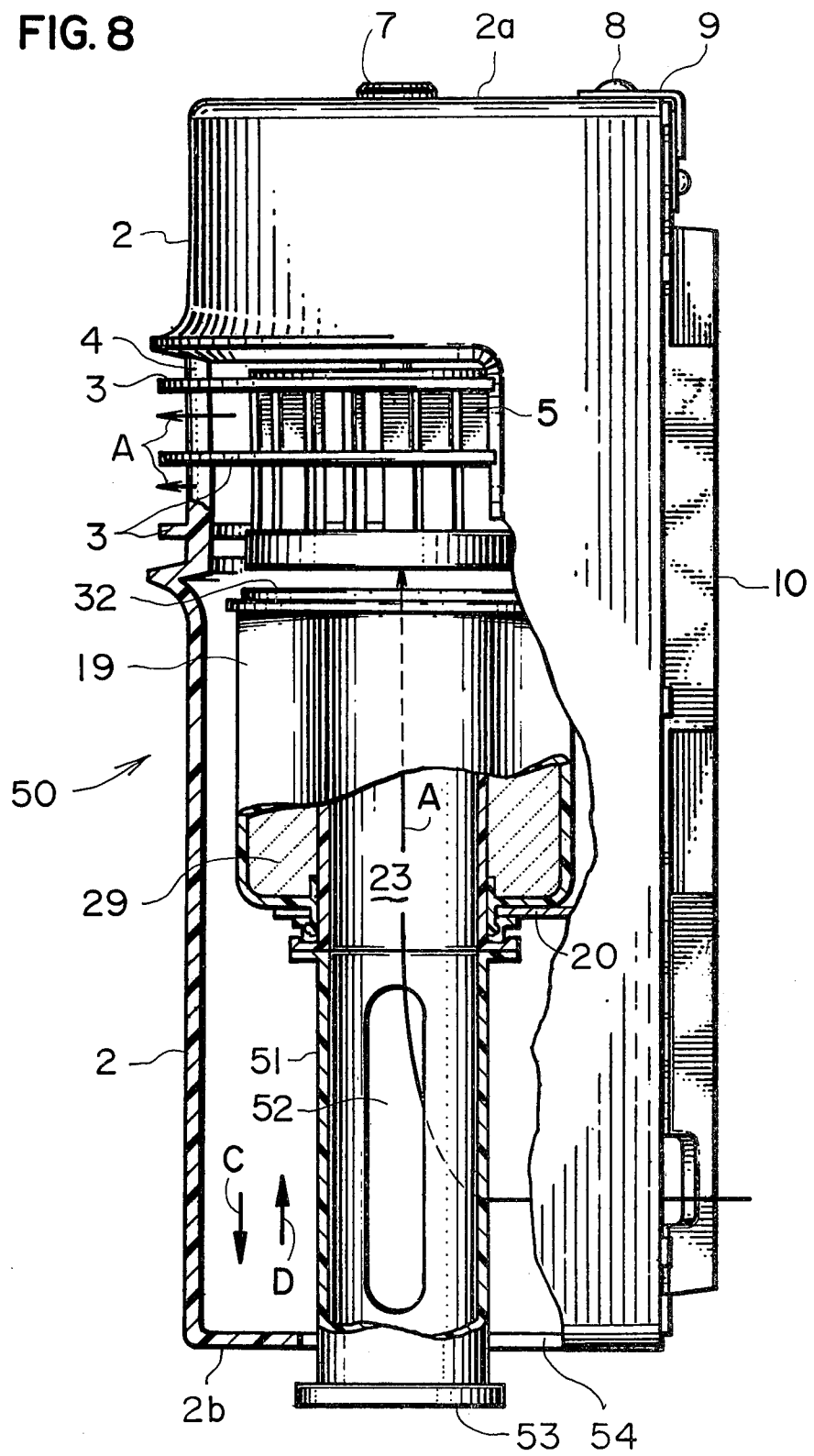

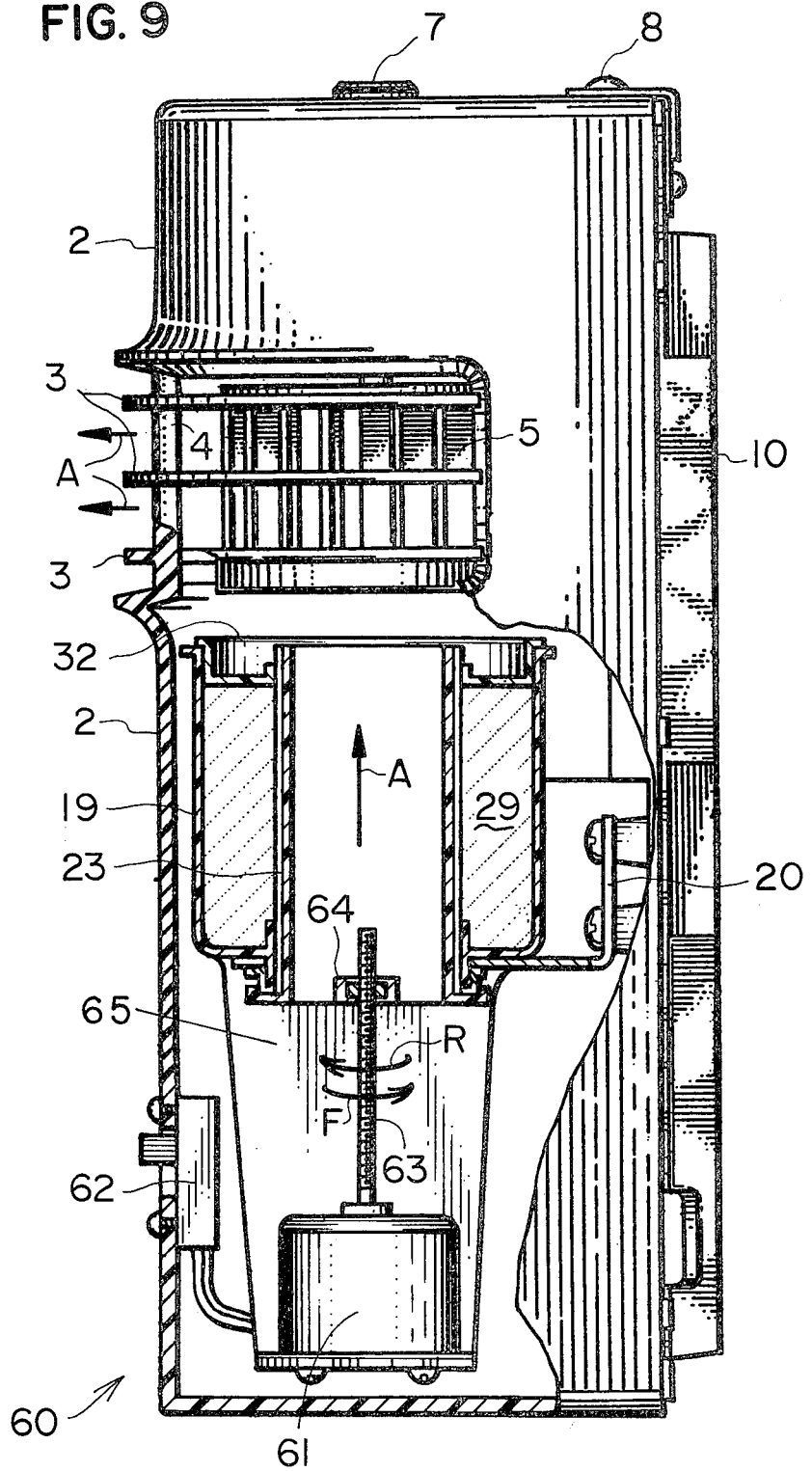

DEVICE FOR EMITTING VOLATILE SUBSTANCE

The present invention relates to a method for emitting volatile substance, and to a device for carrying out the method.

The present invention further relates to a method for adjusting the quantity of volatile substance to be emitted, and to a device for carrying out the method.

The present invention still further relates to a method for maintaining a substantially constant quantity of volatile substance to be emitted for a long period of time, and to a device for carrying out the method.

During recent years, for deodorising rooms or insect-controlling, or in order to send forth fragrance in rooms, suitably covered volatile substance (such as perfume)-impregnated solids or fragrance-emitters have been widely used, which are usually placed in a room to spread its odor by the aid of convection currents of air inside the room. It is known, however, that the intensity of odor of volatile substance emitted from the conventional devices is affected by a change of convection current of air and by a change of humidity, and that they are effective only in an extremely narrow space. Other devices for these purposes have been in practical use, which are intended to spread fragrance over a wider range by the application of the wind to perfume-impregnated solids with an electric fan or the like. In this method, however, a strong wind will promote evaporation of the perfumes which are contained in the solids, and result in shorter persistence of the solids used for deodorising rooms, insect controlling, or other purposes. Furthermore, a serious and fundamental disadvantage with this type of fragrance-emitters is that the intensity of odor of volatile substance emitted from these devices is decreased rapidly as the time proceeds, and that the intensity of odor cannot be adjusted according to the space to be used.

It is an object of the present invention to provide a method for effectively emitting volatile substance, and a device for carrying out the method, while eliminating the above-mentioned disadvantages.

It is another object of the present invention to provide a method for maintaining a substantially constant quantity of volatile substance to be emitted even after a long time use, and a device for carrying out the method.

It is still another object of the present invention to provide a method for freely adjusting the quantity of volatile substance to be emitted, and a device for carrying out the method.

It is still another object of the present invention to provide a method for emitting volatile substance without being affected by a change of environments, i.e., by a change of temperature, humidity or convection current of air inside room, in accomplishing the above-mentioned objects, and a device for carrying out the method.

It is still further object of the present invention to provide a method for effectively and properly emitting volatile substance so as to spread fragrance, and a device for carrying out the method.

It is a still further object of the present invention to provide a method for emitting volatile substance which comprises passing air in one direction into a cylinder inserted into a container wherein is held in place a solid material containing volatile substance, so that air may be in contact with said solid material while passing through said container.

It is a still further object of the present invention to provide a device for emitting volatile substance which comprises a solid material containing volatile substance, a container for holding said solid material, and a cylinder through which air can be passed, and which is adapted to be inserted into said container.

Other features and advantages of the present invention will be apparent to persons skilled in the art from the following detailed description of various embodiments accompanied by the attached drawings wherein identical reference numerals will refer to like parts with respect to construction, function and the like in the various views.

The Drawings

FIG. 8 is a partially cutaway side view of a modification of the device of FIG. 1;

FIG. 9 is a partially cutaway side view of another modification of the device of FIG. 1;

Figure 1:
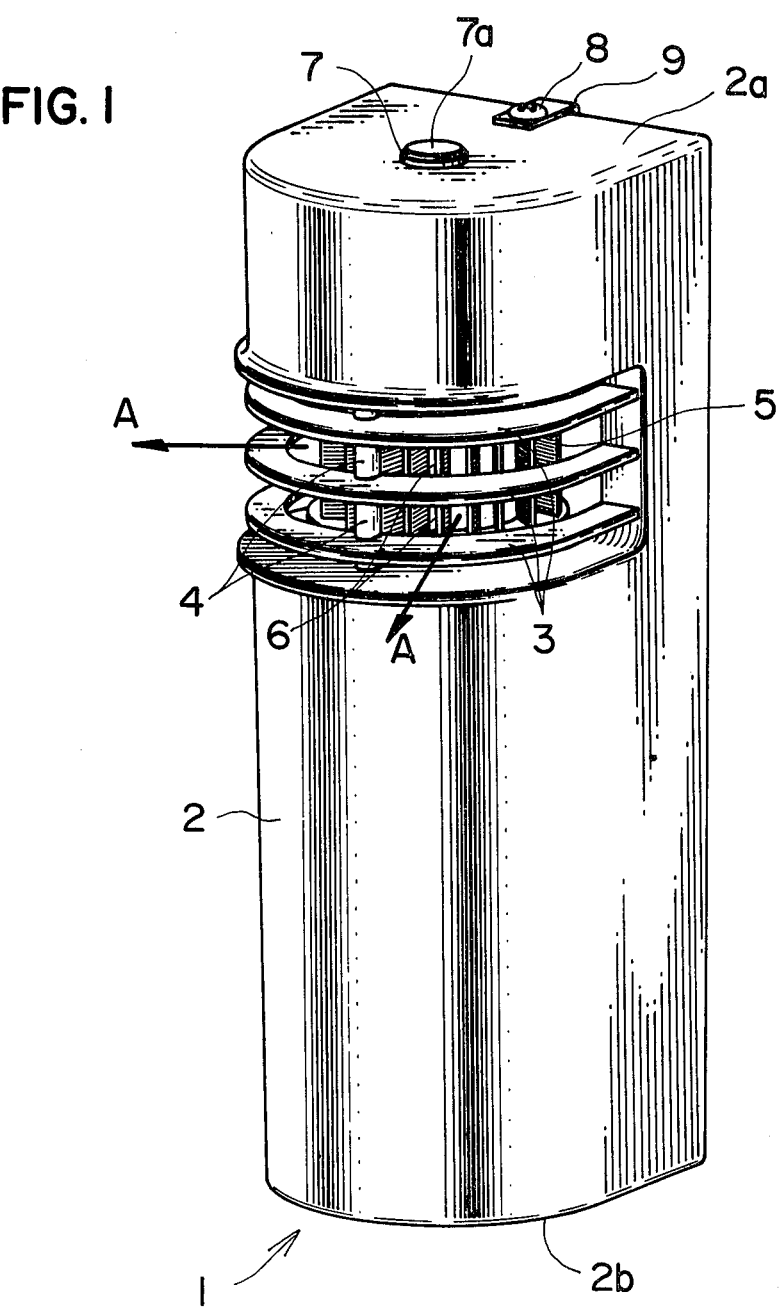
FIG. 1 is a perspective view of an embodiment of a device for emitting volatile substance according to the present invention.
Figure 2:
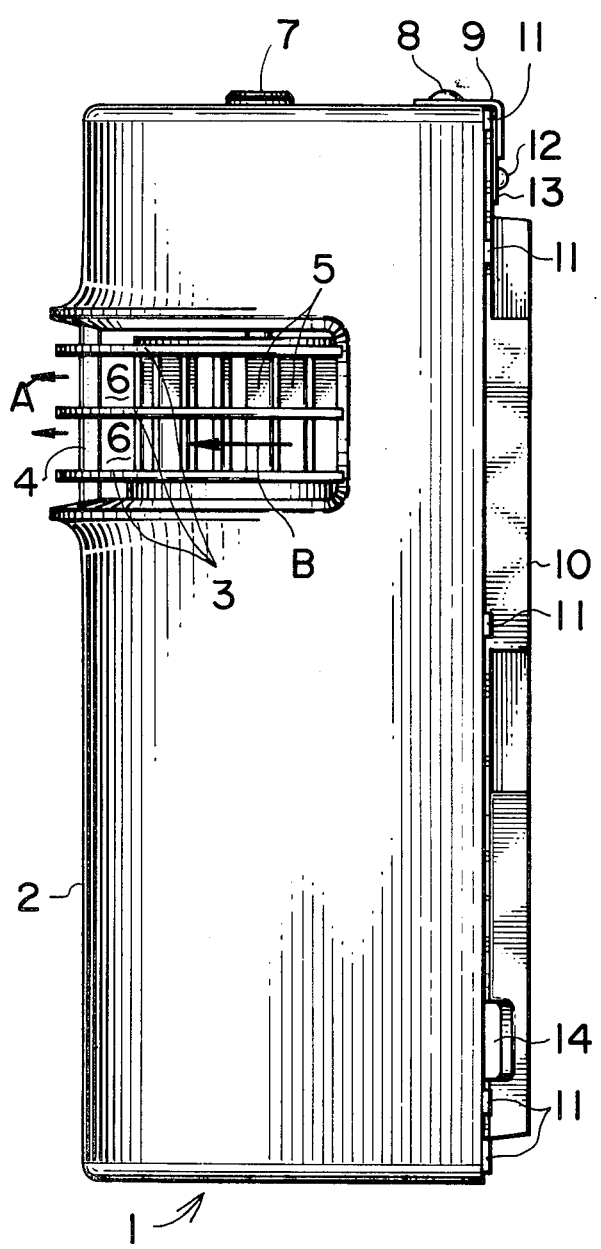
FIG. 2 is a side view of the device of FIG. 1.
Figure 3:
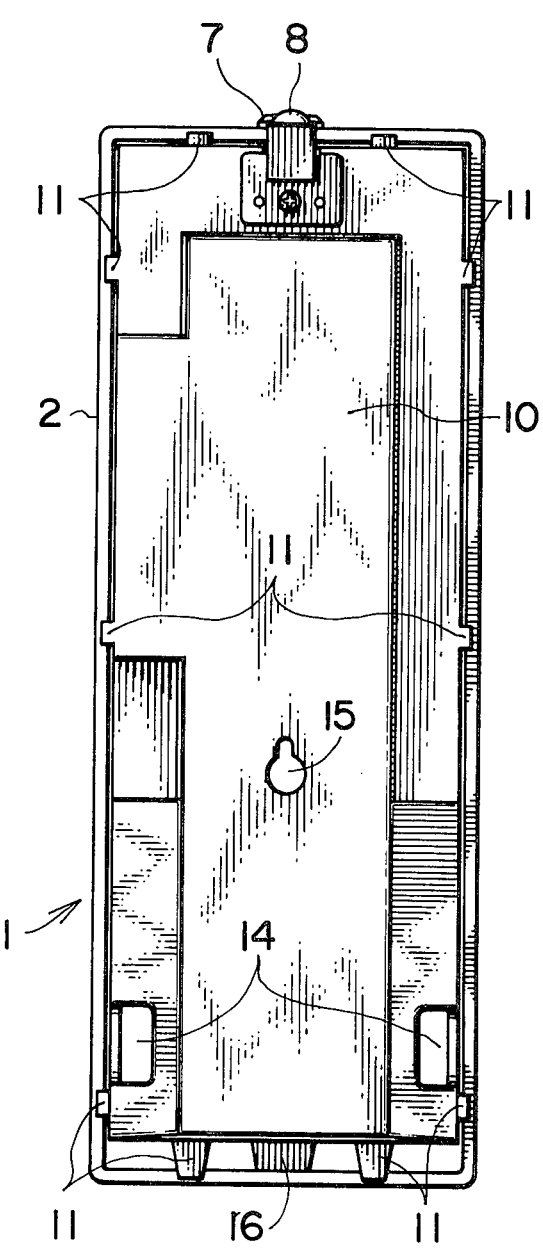
FIG. 3 is a rear view of the device of FIG. 1.
Figure 4:
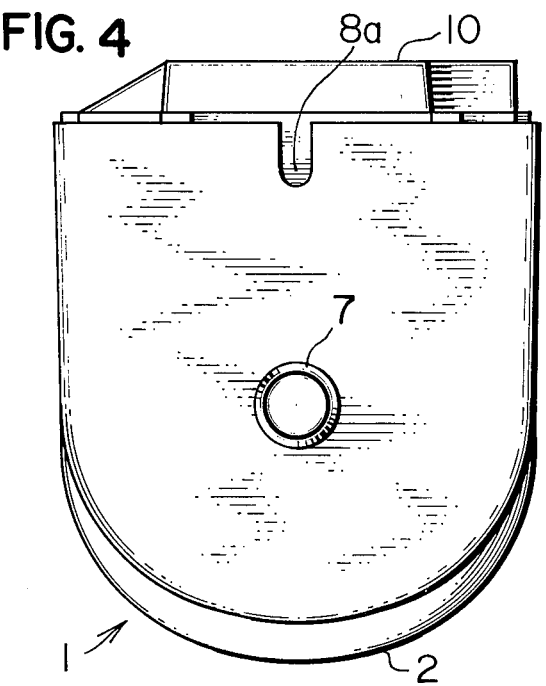
FIG. 4 is a plan view of the device of FIG. 1.

In the drawing, FIGS. 1–6 depict a device 1 for emitting volatile substance, which is formed from metal, or preferably from plastic material which is suitable for integral formation.

Referring to FIGS. 1–4, the emitting device 1 comprises a box-shaped casing 10 which is formed from metal, or preferably from plastic material suitable for integral formation thereof, and a substantially semicylindrical cover 2 having an upper and a lower faces 2a, 2b. Said cover 2 is adapted to be removably secured to said casing 10 by means of a screw 8, a L-shaped metal fitting 9, a plurality of stops 11, and a projection 16, said stops and projection being formed integrally with the casing 10. Furthermore, the cover 2 and the casing 10 are located properly by the stops 11. Said upper face 2a of the substantially semicylindrical cover 2 is provided at its substantially central portion with a port 7a to be covered with a light-permeable lid 7. The rear portion of the upper face 2a has a slot 8a to receive said screw 8. The barrel portion of the substantially semicylindrical cover 2 has an outlet for air containing volatile substance such as perfume. Said outlet is provided with a plurality of curved fins 3 supported by an integrally formed support member 4 and spaced vertically apart to define curved slits 6, through which air containing volatile substance is emitted radially, i.e., in the direction of an arrow A shown in FIG. 1. The casing 10 is provided with a hole 15, thereby permitting the device 1 to be installed on a wall or some other place in a room, and further provided with two slots 14 through which air is drawn into said device 1.

Figure 6:
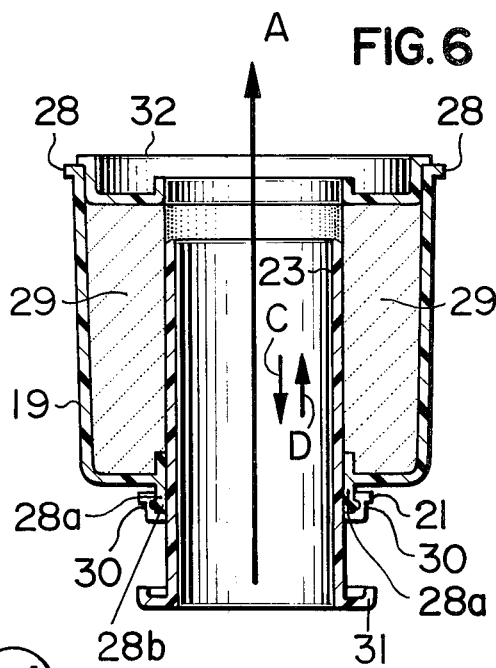
FIG. 6 is a vertical sectional view showing the construction of a part comprising a container, solid material and a cylinder of the device.
Figure 5:
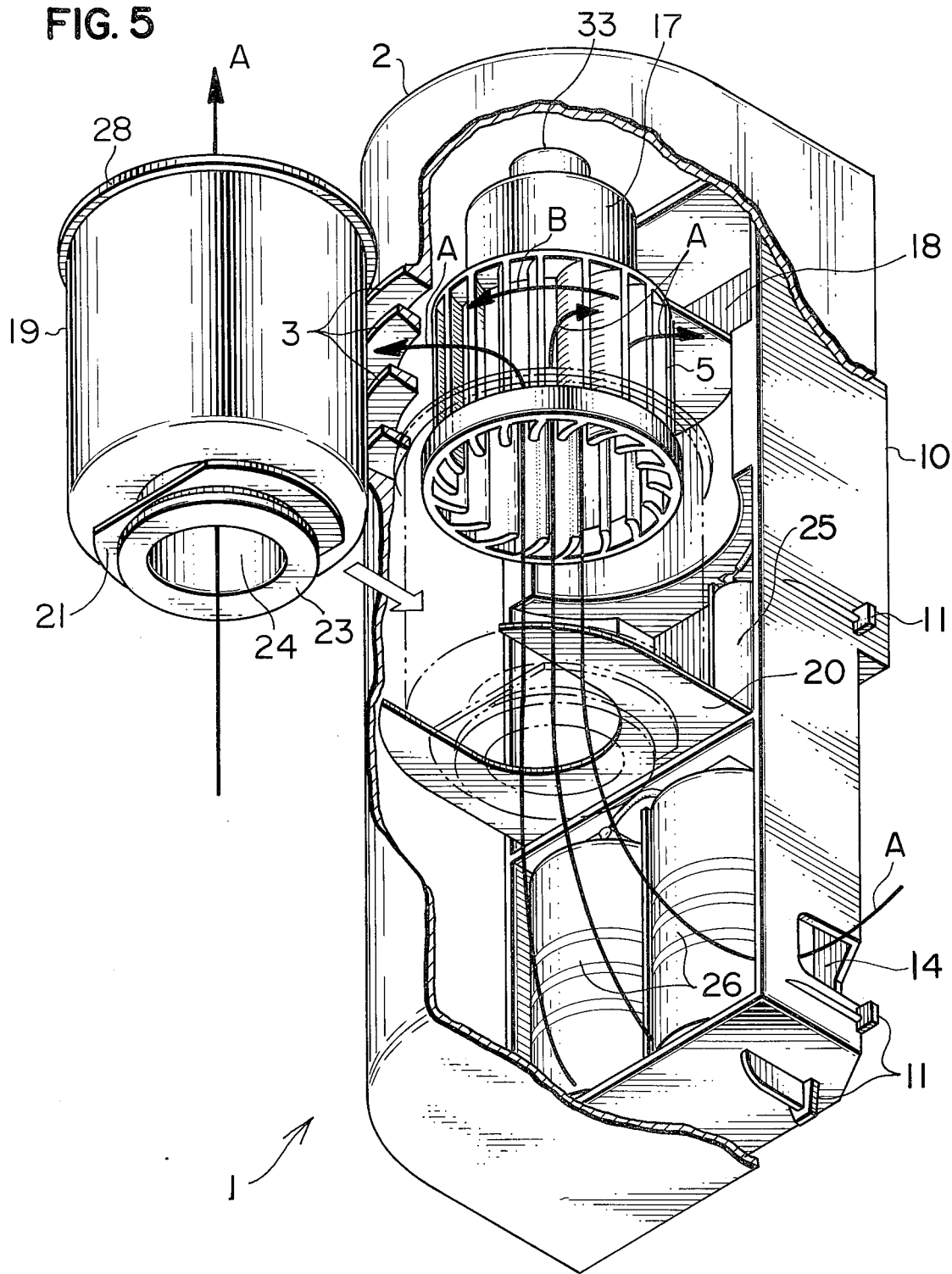
FIG. 5 is a perspective view, partly cut away to show interior construction, of the device of FIG. 1.

Referring now particularly to FIGS. 5 and 6, a motor 17, which is fixed to a metal fitting 18 secured to the casing 10 of the device 1, is driven by an electronic circuit incorporated in the device 1, two dry element cells 26, and a photoelectric element in a photoelectric element case 33. Said photoelectric element case 33 is securely attached to said motor 17, and is located opposite to the port 7a in the upper face 2a. Located beneath said motor 17 is a multi-blade fan 5 generally referred to as a sirocco fan, which is fixed to a shaft of the motor 17 for rotation. The rotation (e.g. in the direction of arrow B shown in FIG. 5) of said multi-blade fan 5 is effected by means of the motor 17, so that air stream designated by an arrow A is produced in the device 1. Said air stream flows from the lower portion of the device 1 toward the upper portion thereof and then to the curved slits 6, as best seen in FIG. 5.

Adjacent the multi-blade fan 5, there is a bowl-shaped container 19 one end of which is a flange 28 for reinforcement, and the other end of which is turned away from the fan 5 and is provided with a cylindrical guide 28a for facilitating the insertion of a cylinder 23. Said container 19 is formed from metal, or preferably from plastic material which is suitable for integral formation, and it holds a cylindrical solid material 29 containing volatile substance such as perfume or deodorising substance therein. Air is passed through the container 19 in the direction of the arrow A shown in FIGS. 5, 6.

Said cylinder 23 is inserted into the container 19 from said guide 28a for up-and-down movement. That is to say, the cylinder 23 is movable in the directions of an arrow C and arrow D, so that an area of contact surface of said solid material 29 with air passing in the direction of the arrow A can be adjusted as needed. One end of the cylinder 23 is also a flange 31 which acts as a stopper for preventing further upward movement of the cylinder 23 relative to the container 19. The cylinder is formed from metal, or preferably plastic material.

There is provided a U-shaped metal fitting 20 acting as a stopper, generally designated by 20, which is secured to the casing 10. A stop member 21, provided with an annular projection 30, is engaged with an annular projection 28b formed on the outer circumferential surface of the free end of the cylindrical guide 28a to prevent the container 19 from moving in correspondence with the movement of the cylinder 23 in the direction of the arrow D, shown in FIG. 6. In other words, even when the cylinder 23 is being inserted into the container 19, the latter can be held in place by the engagement of said stop member 21 with the metal fitting 20. Furthermore, in the casing 10, a dry element cell 25 is incorporated to activate the electronic circuit.

An annular lid 32 is mounted in an airtight fashion on the other end of the container 19 which is turned away from said U-shaped metal fitting 20, whereby the space defined by the container 19 and the cylinder 23 can be made almost completely airtight when the cylinder 23 is completely inserted into the container 19, said space being filled with the solid material 29.

The structure of the part comprising the container 19, the cylinder 23, the solid material 29 and other components is such as to permit easy mounting or demounting to or from the U-shaped metal fitting 20 secured to the casing 10, as shown in two dots-and-dash lines in FIG. 5.

Figure 7:
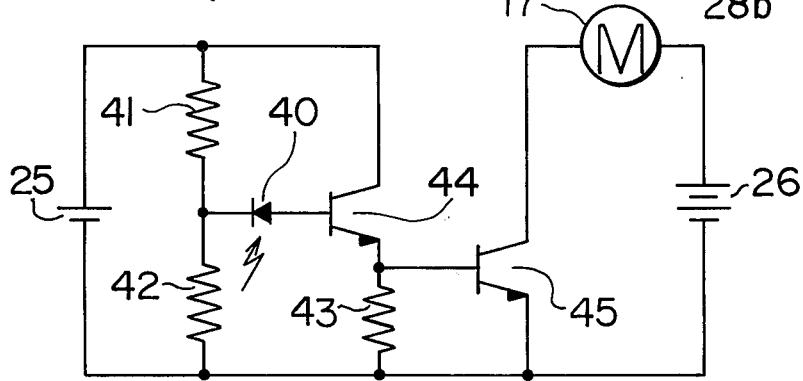
FIG. 7 shows a circuit diagram of one form of electric circuit to be incorporated in the device shown in FIG. 1.

Referring now to FIG. 7, there is shown one form of an electric circuit incorporated in the device 1, which comprises said dry element cells 25, 26, resistances 41, 42, 43, said photoelectric element, e.g., a photodiode 40, transistors 44, 45, and said motor 17.

The manner of operation of the device 1 will be described with reference to FIGS. 1 to 7. Before getting to the description, it is to be understood that the multi-blade fan 5 may be rotated all the time by a means well known in the electric art, but it may be preferably rotated only at a predetermined time and/or under predetermined conditions, as described in the following. Light of a room lighting is applied to the photodiode 40 through the port 7a, so that the transistor 44 is turned "ON" and then the other transistor 45 is also turned "ON." Consequently, the motor 17 is supplied with electric power from the dry element cells 26, i.e., activated so as to rotate the fan in the direction of the arrow B, whereupon air flows upward relative to the device 1 through the cylinder 23 and then is radially released through the curved slits 6 into the atmosphere. The intensity of odor of the volatile substance emitted from the device 1 is adjustable by properly locating the cylinder. That is, since the intensity of odor changes in proportion to the area of contact surface of the solid material with air, the cylinder 23 is moved in the direction of the arrow C to increase the intensity of odor, while it is moved in the direction of the arrow D to decrease it. It is considered an important feature of the present invention that the intensity of odor is not affected by a change of wind velocity caused by a change of voltage of the dry element cells 25, and that there is not very much change of the intensity of odor by the lapse of time, since the exposed surface area of the solid material 29 is comparatively small with respect to its volume. Furthermore, when the cylinder 23 is inserted into the container 19 to such an extent that it slightly protrudes beyond the annular lid 32, the container 19 is made completely airtight, thereby permitting the evaporation of perfume to be stopped. This means that there is no need of special wrapping of the container 19 for the purpose of preventing the evaporation of perfume, for example for transporting and storing the container 19. In short, a user can easily control the intensity of odor by properly locating the cylinder 23.

A modification of the device 1 for emitting volatile substance according to the present invention will be described by referring to FIG. 8. A device 50 for emitting volatile substance is identical with the first embodiment described above, except that there is further provided a control cylinder 51 provided with a plurality of slits 52 through which air flows in the longitudinal direction with respect to the device 50 and fitted in a U-shaped slot 54 in the bottom face 2b of the cover 2. One end of said control cylinder 51 is secured to the cylinder 23, while the other end thereof is provided with an annular projection 53 to be gripped by hand. It will be observed, therefore, that in the device 50, the intensity of odor, i.e., an area of contact surface of the solid material 29 with air can be adjusted by manually moving the control cylinder 51 either in the direction of the arrow C or the arrow D. The device 50 eliminates the need of removing the cover 2 from the casing 10, and therefore it is very convenient for use.

Figure 10:
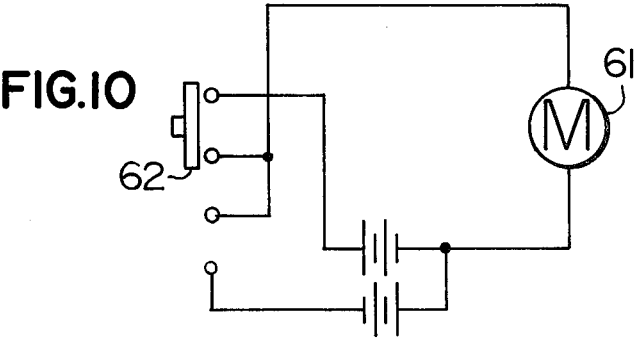
FIG. 10 shows a circuit diagram of one form of electric circuit to be incorporated in the device shown in FIG. 8.

A further modification of the present invention will be described by referring to FIG. 9. The structure of a device 60 for emitting volatile substance is such that the intensity of e.g. odor of volatile substance can be adjusted automatically. The device 60 includes a switch 62 such as a slide switch, a rotary switch or the like mounted on the front portion of the cover 2; a threaded member 64 secured to the cylinder 23, a reversable motor 61 to be activated by a said switch 62, and to be mounted on the mounting plate 65 secured to or integrally within the container 19 for disposing it in concentric relation therewith and a shaft 63 of said motor 61 the screw portion of which is adapted to be threadedly engaged with said threaded member 64, said threaded member 64, said motor 61 and said shaft 63 being arranged not to block the upwardly flowing air stream relative to the device 60. It is natural that said switch 62 should be in linkage with said motor 61 by a means well known in electric art, as shown in FIG. 10. Said dry element cells 26 may be used as power source for said motor 61. Therefore, when said switch 62 is turned "ON" in a predetermined manner, the shaft 63 of the motor 61 is either rotated in the direction of an arrow F to effect downward movement of the cylinder 23 relative to the device 60, or is rotated reversely, i.e., in the direction of an arrow R to effect upward movement thereof relative to the device, thereby permitting the intensity of odor to be adjusted automatically.

Having thus described in detail various embodiments of the device for emitting volatile substance according to the present invention, it will be appreciated that persons skilled in the art will be able to further modify certain of the structure which has been illustrated and to substitute equivalent elements for those disclosed while continuing to practice the principle of the present invention, and it is, therefore, intended that all such modifications and substitutions be covered as they are embraced within the spirit and scope of the present invention.

What is claimed is:

1. A device for emitting volatile substance which comprises:
   a casing having a plurality of openings through which air can pass;
   a motor on said casing;
   a fan connected to the motor for forcing air through said openings;
   a container mounted on the casing and having a pair of open ends;
   a tubular adjusting member slidably mounted in one of the open ends of the container, the tubular adjusting member having an open end positioned within the container and an axially extending passage through which air can pass;
   and a volatile substance within the container and outwardly of the tubular adjusting member, the adjusting member being slidable axially within said one open end of the container to vary the spacing of said open end of the adjusting member from the other open end of the container whereby the amount of volatile substance exposed to air flowing from said open end of the adjusting member can be varied.

2. The structure of claim 1 in which the container includes a pair of end walls each of which has an opening to provide said pair of open ends, the tubular adjusting member being slidable through the openings and engageable with the end walls to seal the volatile substance within the container.

3. The structure of claim 1 including a mounting fitting on the casing, the container being removably mounted on the mounting fitting.

4. The structure of claim 1 including a control cylinder connected concentrically with the tubular adjusting member and extending out of the casing whereby the tubular adjusting member can be moved with respect to the container by moving the control cylinder.

5. The structure of claim 1 in which the container includes a cylindrical guide portion concentric with and slidably engaging the tubular adjusting member, an end wall extending radially outwardly from the guide portion, and a stop member extending radially outwardly from the guide member and spaced axially from the end wall, the casing including a mounting fitting which extends into the space between the stop member and the end wall of the container to removably mount the container.

6. The structure of claim 1 including a reversible motor within the casing having a threaded drive shaft threadedly engaged with the tubular adjusting member along the axis thereof whereby the tubular adjusting member can be moved axially with respect to the container by the reversible motor.

7. The structure of claim 1 including photoelectric means on the casing for energizing the motor.

* * * * *